US010337761B2

(12) United States Patent
Blackstone (10) Patent No.: US 10,337,761 B2
(45) Date of Patent: Jul. 2, 2019

(54) MICROENVIRONMENTAL COOLING SYSTEM

(76) Inventor: Ralf W. Blackstone, Clearwater, FL (US)

( * ) Notice: Subject to any disclaimer, the term of this patent is extended or adjusted under 35 U.S.C. 154(b) by 393 days.

(21) Appl. No.: 13/204,328

(22) Filed: Aug. 5, 2011

(65) Prior Publication Data

US 2012/0011873 A1 Jan. 19, 2012

Related U.S. Application Data

(63) Continuation-in-part of application No. 12/004,732, filed on Dec. 21, 2007, now abandoned.

(60) Provisional application No. 61/371,009, filed on Aug. 5, 2010.

(51) Int. Cl.
| | |
|---|---|
| *F24F 13/30* | (2006.01) |
| *F28D 1/02* | (2006.01) |
| *F28D 1/047* | (2006.01) |
| *F28F 1/32* | (2006.01) |
| *A61F 7/00* | (2006.01) |
| *F28F 1/12* | (2006.01) |
| *A62B 17/00* | (2006.01) |

(52) U.S. Cl.
CPC .............. *F24F 13/30* (2013.01); *F28D 1/024* (2013.01); *F28D 1/0477* (2013.01); *F28F 1/32* (2013.01); *A61F 7/0085* (2013.01); *A62B 17/005* (2013.01); *F25D 2400/26* (2013.01); *F28F 1/12* (2013.01); *F28F 2215/00* (2013.01)

(58) Field of Classification Search
CPC ......... F25D 2400/26; F24F 13/30; F24F 1/02; A62B 17/005; A61F 7/0085; F28F 2215/00; F28F 1/12; F28D 7/1661; F28D 7/1607; F28D 7/1623

USPC .................................................. 165/181, 159
See application file for complete search history.

(56) References Cited

U.S. PATENT DOCUMENTS

| | | | |
|---|---|---|---|
| 732,945 | A | 7/1903 | Jensen ............................ 62/255 |
| 1,170,658 | A | 2/1916 | Mitchell .......................... 62/310 |
| 1,690,417 | A | 11/1928 | Lundmark ...................... 62/425 |
| 1,739,672 | A * | 12/1929 | Higgins ................... F28F 1/325 |
| | | | 165/151 |
| 2,093,834 | A | 9/1937 | Gaugler |
| 2,133,818 | A | 10/1938 | Hulse .............................. 62/419 |
| 2,207,956 | A | 7/1940 | Timms et al. |

(Continued)

FOREIGN PATENT DOCUMENTS

| | | | | |
|---|---|---|---|---|
| DE | 20213753 | * | 2/2003 | ............. A63B 22/08 |
| FR | 2679017 A | | 1/1993 | |

(Continued)

OTHER PUBLICATIONS

Tu, Fitness Equipment with Air Conditioning, Mar. 13, 2003, EPO, DE 20213753, all.*

*Primary Examiner* — Filip Zec
(74) *Attorney, Agent, or Firm* — Jackson Walker LLP (57) ABSTRACT

A microenvironmental cooling system is disclosed. The microenvironmental system includes a pressure box or a pressure source upstream of an evaporator. Downstream of an evaporator is a personal cooling device, which is adapted to lay adjacent or on the skin of the user. The evaporator includes an evaporator coil (having fins and a coolant tube) and a housing and walls configured to direct the airflow through the housing, in several embodiments, multiple times across the longitudinal axis fins of the coil.

20 Claims, 7 Drawing Sheets

(56) References Cited

U.S. PATENT DOCUMENTS

| | | | |
|---|---|---|---|
| 2,452,594 A | 11/1948 | Nathan | 62/78 |
| 2,453,017 A | 11/1948 | Kaufman | |
| 2,502,675 A * | 4/1950 | Simpelaar | F28D 7/06 165/159 |
| 2,668,962 A | 9/1954 | Summers | |
| 2,780,073 A | 2/1957 | Curry | 62/244 |
| 3,468,299 A | 9/1969 | D-Amato | |
| 3,496,703 A | 2/1970 | Maguire et al. | |
| 3,498,076 A | 3/1970 | Michael | |
| 3,590,913 A * | 7/1971 | Tschudin | E06B 3/6715 165/104.19 |
| 3,777,506 A | 12/1973 | Hergatt et al. | |
| 3,809,151 A | 5/1974 | Scheidel et al. | |
| 3,961,496 A | 6/1976 | Ku | |
| 4,055,173 A | 10/1977 | Knab | |
| 4,129,013 A * | 12/1978 | Hine, Jr. | 62/285 |
| 4,170,998 A * | 10/1979 | Sauder | A61F 7/02 607/104 |
| 4,194,247 A * | 3/1980 | Melander | A41D 13/0025 2/457 |
| 4,557,320 A | 12/1985 | Allen | |
| 4,566,890 A * | 1/1986 | Hostler | C03B 37/02 134/198 |
| 4,586,346 A * | 5/1986 | St-Pierre | F25D 17/04 62/259.1 |
| 4,777,802 A | 10/1988 | Feher | |
| 4,998,415 A * | 3/1991 | Larsen | 62/231 |
| 4,998,418 A | 3/1991 | Fatigati | |
| 5,014,355 A | 5/1991 | Vollenweider | |
| 5,042,474 A | 8/1991 | Williamson | |
| 5,062,424 A | 11/1991 | Hooker | |
| 5,115,859 A | 5/1992 | Roebelen et al. | |
| 5,193,347 A * | 3/1993 | Apisdorf | A42B 3/285 2/171.3 |
| 5,197,301 A | 3/1993 | Holcomb | |
| 5,431,022 A | 7/1995 | Abe | 62/4 |
| 5,450,894 A | 9/1995 | Inoue et al. | |
| 5,482,113 A * | 1/1996 | Agonafer | F28D 1/024 165/122 |
| 5,553,354 A | 7/1996 | Trulaske, Sr. | |
| 5,572,991 A | 11/1996 | Grilliot et al. | |
| 5,588,153 A | 12/1996 | Ignon et al. | |
| 5,655,374 A | 8/1997 | Santilli et al. | |
| 5,685,165 A | 11/1997 | Bigelow | |
| 5,733,318 A | 3/1998 | Augustin | |
| 5,970,519 A | 10/1999 | Weber | |
| 6,105,382 A * | 8/2000 | Reason | 62/259.3 |
| 6,146,412 A | 11/2000 | Van Duren | 607/107 |
| 6,170,282 B1 | 1/2001 | Eddins | |
| 6,243,892 B1 | 6/2001 | Kelling | |
| 6,257,011 B1 | 7/2001 | Siman-Tov et al. | |
| 6,263,510 B1 | 7/2001 | Bay et al. | |
| 6,269,651 B1 | 8/2001 | Price | |
| 6,272,877 B1 | 8/2001 | Halloran | |
| 6,318,108 B1 * | 11/2001 | Holstein | F24F 1/06 62/279 |
| 6,354,099 B1 * | 3/2002 | Bieberich | 62/259.3 |
| 6,519,964 B2 | 2/2003 | Bieberich | |
| 6,568,202 B1 * | 5/2003 | Hodges | 62/306 |
| 6,571,574 B1 | 6/2003 | Blackstone | |
| 6,688,128 B1 | 2/2004 | Robbie et al. | |
| 6,715,309 B1 | 4/2004 | Junkins | |
| 6,792,702 B2 | 9/2004 | Borsoi et al. | |
| 6,901,769 B2 | 6/2005 | Blackstone | |
| 6,942,015 B1 | 9/2005 | Jenkins | |
| 6,971,249 B1 | 12/2005 | Blackstone | |
| 6,993,930 B2 | 2/2006 | Blackstone | |
| 7,243,711 B2 * | 7/2007 | Amstutz | F28D 7/163 165/159 |
| 7,266,965 B2 | 9/2007 | Blackstone | |
| 7,266,966 B2 | 9/2007 | Blackstone | |
| 2002/0056281 A1 | 5/2002 | Bieberich | |
| 2002/0058975 A1 | 5/2002 | Bieberich | |
| 2003/0029182 A1 | 2/2003 | Augustine et al. | |
| 2003/0079488 A1 | 5/2003 | Bieberich | |
| 2003/0229385 A1 * | 12/2003 | Elkins | 607/104 |

FOREIGN PATENT DOCUMENTS

| | | |
|---|---|---|
| GB | 200335 A | 7/1923 |
| JP | 58153028 A | 10/1983 |
| WO | WO 98/03091 A | 1/1998 |

\* cited by examiner

MICROENVIRONMENTAL COOLING SYSTEM

This application claims the benefit of and priority from, and incorporates by reference U.S. Patent Application No. 61/371,009, filed Aug. 5, 2010. This application also incorporates by reference U.S. patent application Ser. No. 12/004,732, filed Dec. 21, 2007.

FIELD OF THE INVENTION

Heat exchanger based systems for use with personal cooling devices.

BACKGROUND OF THE INVENTION

Achieving human comfort by microenvironmental means is not a new concept. Man has been doing it for eons every time he wore a bearskin in his cave to protect himself against the cold or a coat against the chill of a winter's night in more modern times. These achieve warmth for the wearer because they prevent cool airflow from the outside reaching the skin of the user. Thus the trapped air is warmed by the body heat to near body temperature and the person feels comfortable. However, these garments must also 'breathe' and allow a small amount of escape of that warmed air in order to allow the skin's perspiration and its humidity to also escape. Otherwise that moisture is trapped against the skin and keeps the pores of the skin from allowing their moisture to escape effectively. This means our primary mechanism for regulating body temperature (sweating) is inhibited and the person will shortly become uncomfortable.

While microenvironmental heating is something man has done for millions of years, microenvironmental cooling is new. Do you really care what temperature exists in the back corner of the room on a hot summer's day? No, you only care about the 1-inch of air immediately surrounding you skin. You care not only about its temperature, but also about its humidity.

Heat Index is the 'feels like' temperature in hot conditions. It's primary components are ambient temperature and humidity. A 90° F. temperature with 40% humidity has a Heat Index "feels like" temperature of 91° F. Raise that humidity level to 90% and the Heat Index rises to 121.9° F. Raise both temperature and humidity to 100° F. and 100% humidity and the Heat Index is 195.3° F. Thus humidity, more that heat itself, is the primary driver of increased Heat Index and heat discomfort.

Whether the air is moving or still is not considered to be a component of Heat Index. Yet anyone working in hot humid conditions knows hot conditions in still air are far more miserable than the same conditions with a 2-3 mph breeze.

The human body's primary means for internal temperature regulation is sweating (transpiration) where body water is put out through the skin's pores as water or water vapor and so rids the body of its internal excess heat. As humidity rises, the gradient between the skin's pores and the outside environment is reduced finally to the point where water vapor can no longer flow from the skin to the outside (at 100% relative humidity). Now the body is inefficient at ridding itself of its heat, and heat begins to build up, causing more sweating as formation of liquid on the skin in an effort to rid the body of its excess heat.

If that person is in still air and the same relative position for long periods of time (as walking will cause the air and its heat/humidity in contact with the skin to move off the skin), his immediate environment becomes saturated with his own body moisture, either as liquid or humid vapor at his body temperature, Regardless of the actual temperature, the 1-inch of air immediately around him becomes nearly 100% humid and at (or even above) his core body temperature. If even a slight 2-3 mph breeze then begins to blow upon him, that humid vapor is blown away from him and he immediately begins to feel relief. His ability to transpire effectively is restored and he begins to feel cooler immediately with both his immediately surrounding temperature and humidity dropping as his personal Heat Index plummets. Comfort is restored.

Air-conditioning of indoor air began in the early 20th Century and is a comfort familiar to us all. Yet certain jobs and outdoor activities leave us uncomfortable as air-conditioning is not possible. Outdoor jobs, work in warehouses where air-conditioning is impractical, work in confining work clothes where one cannot feel air-conditioning such as a gowned surgeon at surgery, workers in HazMat or Bio-Hazard total enclosure suits, firemen, furnace workers, flight-line workers, etc. all share hot sweaty work conditions as the working conditions prevent them from experiencing proper air-cooling. That is—until now.

SUMMARY OF THE INVENTION

Microenvironmental air-cooling (as opposed to air-conditioning which employs both heating and cooling to provide comfortable conditions for its users) brings the advantages of air-cooling to the personal space of workers previously denied such comfort by their job. The primary components of microenvironmental air-cooling (MAC) are a pressurized evaporator coil engineered (for a specified temperature range) to take the hot ambient air and produce an airstream of the desired final temperature in a single pass through the evaporator. Implicit in this MAC is a reduced but pressurized airflow through a properly sized evaporator through one of the alternate airflow paths attached and hereafter described. Pressurization is necessary to drive the airflow through these longer and more resistive alternate pathways, but the advantage is much higher heat extraction from the airflow and thus much colder air than can normally be produced by an air conditioner (14-17° F.$\Delta$T in a regular air-conditioner, currently 80° F. $\Delta$T in one of our working prototypes).

Also implicit in this assembly is an end-user device capable of confining the hyper-cold limited airflow to the 1-inch of space immediately upon the skin of the end-user (especially his trunk, head, and neck). This device must also make use of the pressurization to effect jets at critical points of the body (such as the armpits, neck, scalp, and back) and so create that 2-3 mph breeze inside the end-user device (such as a vest, a jacket (or other garment), a comforter, a total-enclosure suit, a shell over a cot, etc.). Thus the end-user can utilize the limited cold air to effectively cool his personal microenvironment.

As alternate pathway evaporators generate far colder than usual air-conditioning evaporators, there is a far greater propensity for condensation to form within these MAC evaporators. As these alternate pathway evaporators are sealed and pressurized, that condensate must be collected and drained from the evaporator so a water-trap obstruction cannot form (see, for example, FIG. 3). Because these alternate airflow evaporators are maintained near 0° C. (32° F.), that condensate can be copious. As draining such an amount may be otherwise messy, that condensate can be blown onto the condenser fins, thus increasing their cooling efficiency and adding to the overall efficiency of the system.

Implicit, but not obvious, is the last advantage of microenvironmental air-cooling via these alternate airflow pathways. Because humidity in the hot air condenses out within the evaporator as drainable water, the final air output is far drier than surrounding ambient air. Applicant has reduced 90% humidity ambient air to 36% humidity after a single pass through our prototype evaporator. As humidity is the most important component of Heat Index to comfort, this stripping of humidity from the microenvironmental airflow is THE factor that produces the greatest comfort for the end-user, much more than standard air-conditioning is capable of producing.

DETAILED DESCRIPTION OF THE PREFERRED EMBODIMENT

Figure 1:
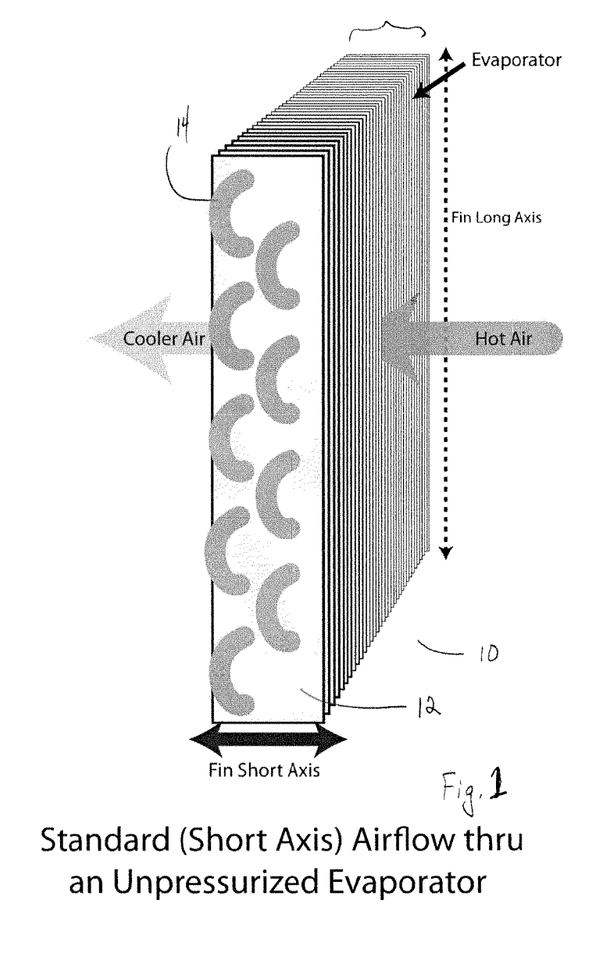
FIG. 1 is a side perspective view of a standard short axis airflow through an unpressurized evaporator.

FIG. 1 illustrates the prior art showing an evaporator coil 10 having fins 12 and cooling tubes 14 engaged therewith. Hot air is seen making a single pass blowing from the right to the left across or parallel to the fin short axis.

Figure 2A:
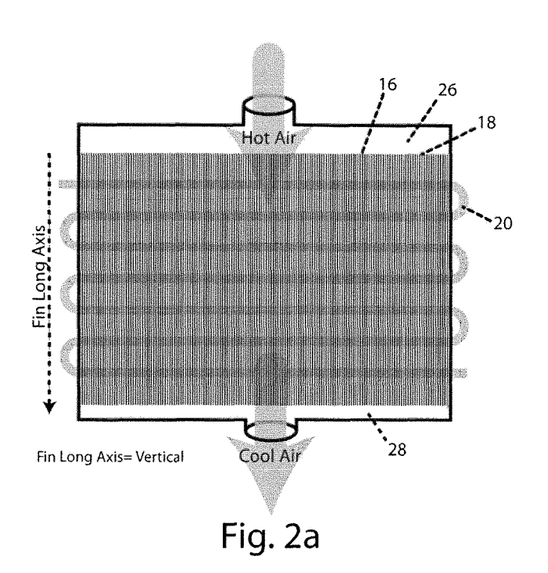
FIGS. 2A and 2B are side elevational view and perspective view, respectively, of a vertical embodiment of Applicant's evaporator for use with a pressurized ambient air source and a personal air cooling device.
Figure 2B:
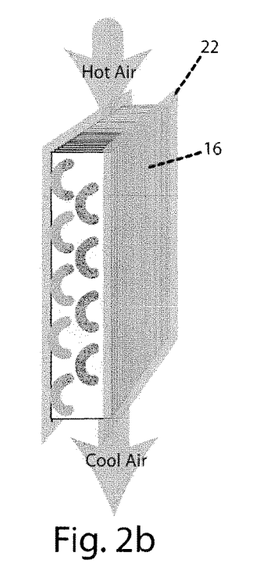

FIGS. 2A and 2B illustrate an embodiment of Applicant's evaporator 15. This embodiment uses evaporator coil 16 oriented with gravity so that the fin long axis is substantially vertical. Air flows along (not across) the long axis of the fins, in a single pass. Further, air, typically hot air coming in from the top, makes a single pass and exits a housing or encasement typically near the bottom thereof. At least some walls 22, which may be walls of a housing or encasement, are placed adjacent the two opposed side edges of the vertically oriented coil so as to constrain the air moving from top to bottom as seen in FIG. 2B. Plenums 26/28 and a housing 24 as set forth in more detail below may be used with this embodiment.

Figure 3:
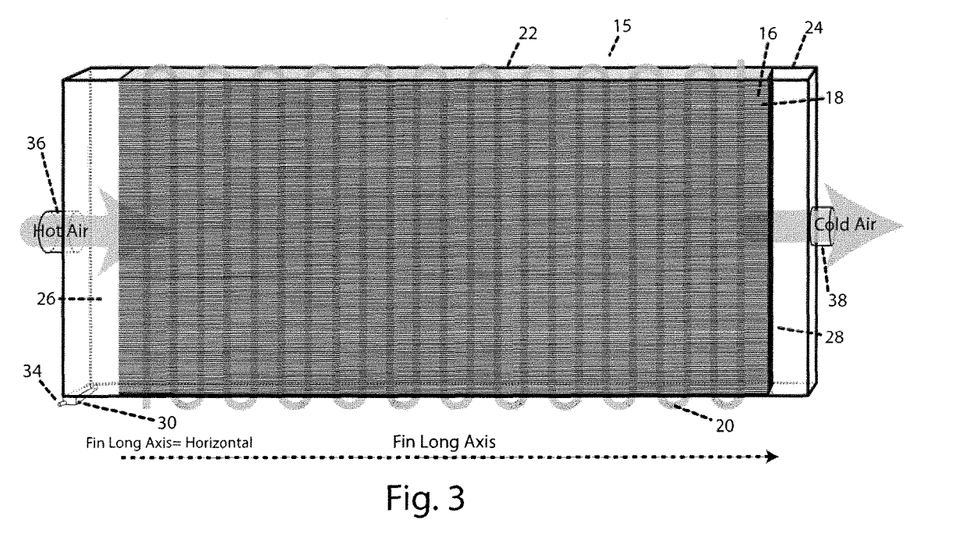
FIG. 3 illustrates a side view in perspective of an alternate preferred embodiment of Applicant's evaporator.

In FIG. 3, another embodiment of Applicant's evaporator 15 is illustrated. In the embodiment of FIG. 3, evaporator coil 16 is placed so that fins 18 are horizontal (vertical and horizontal with respect to gravity). Coolant tubes 20 are generally engaged through the fins as illustrated in the Figures. Here, walls 22 may be provided again to restrict the air to a single pass, illustrated in FIG. 3 from left to right, horizontally along (not across) the long axis of the horizontal fins. Walls 22 may be some of the walls of an encasement or housing 24.

The embodiment of FIG. 3 has an horizontal fin axis as compared to the embodiment of FIGS. 2A and 2B, which has a vertical fin axis. Both embodiments constrain airflow to a single pass, along (not across) the fins. Moreover, the airflow is pressurized with a fan or a pressure source upstream of the inlet and therefore evaporator coil 16 is usually placed in an encasement or housing 24 with inlet 36 on an upstream side for receiving pressurized warm (ambient) air and an outlet 36 on a downstream side adjacent where cold air exits the evaporator 15 for providing cold pressurized air to a personal cooling device downstream thereof as set forth in more detail below.

Cooled warm air will typically generate some condensate and, in FIGS. 2A and 2B, the condensate may move downward, under the impetus of gravity, to collection tubes as set forth herein below. While the embodiment of FIG. 3 is generally provided vertically, it may be tilted a few degrees from the orientation illustrated in FIG. 3 to help condensate flow off the edges thereof.

FIG. 3 also illustrates the use of encasement or housing 24, typically six walls surrounding the coil 16, which walls are substantially airtight and may include upstream plenum 26 having inlet 36 for receipt of warm pressurized air and may also include downstream plenum 28 with outlet 38, which plenum will collect the now cooled air and send it out outlet 38 for use in a personal air cooling device downstream thereof.

Housing or encasement 24 may also include at the bottom thereof, a catch basin 30 which walls may be angled and may have a collection tube 32 with a multiplicity of small holes at the base thereof. A drain 34 may engage the catch basin and/or the collection tube for draining condensate that will typically be generated as the warm air cools as it moves left to right through the airtight encasement. Encasement or housing 24 will typically have walls adjacent the short axis to the fins so air will be constrained to move from left to right as illustrated in FIG. 3, or top to bottom as illustrated in FIGS. 2A and 2B, which also can have a similar encasement, plenum, drain, etc.

Figure 4:
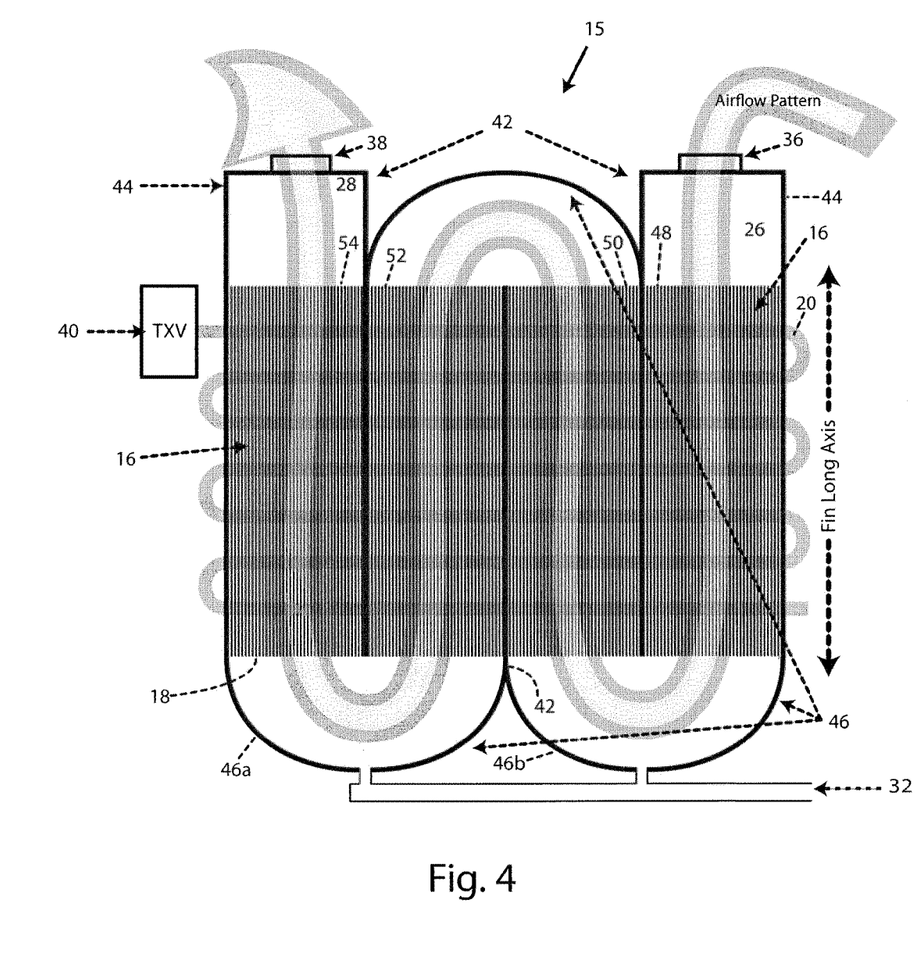
FIG. 4 illustrates a side view of another alternate embodiment of Applicant's evaporator.

FIGS. 2A, 2B, and 3 all illustrate long axis flow of pressurized air. Likewise. FIG. 4 illustrates the long axis of the airflow along the fins. FIG. 4 illustrates, in addition to evaporator coil 16 with coolant tubes 20 and fins 18, that a refrigerant thermostatic expansion valve 40 or capillary tube is typically used, as known in the art, to control the expansion of the coolant agent entering the evaporator coil 16. Walls 22 are omitted, but are similar to the walls 22 of FIGS. 2A and 2B, in that they will help constrain the airflow. However. FIG. 4 uses typically a plurality of dividers 42 and/or airflow redirectors 46, which will help constrain and direct the flow between endplates 44 so multiple passes are made up and down the long axis of vertically oriented fins. An upstream plenum 26 may be provided as illustrated in FIG. 4, as well as an inlet 36 for receiving warm ambient air and outlet 38 for expelling cool, drier air. Airflow redirectors 46 may engage the endplates and at least some of the dividers (alternate dividers as illustrated in FIG. 4), so as to allow multiple passes of the airflow with the long axis of the fins, noting however that the multiple passes are not multiple passes of the same air molecules on the same fins, but are passes through the sections 48/50/52/54 of the evaporator coil 16 as illustrated in FIG. 4. Dividers 42 typically represent common walls. Note that airflow redirectors 46a/46b are located adjacent the bottom of the vertically oriented fins 18. Under the impetus of gravity, condensate may form near the bottom of the airflow redirectors 46a/46b or other lower walls and thus as in the previous embodiments, a collection tube 32 with many small holes may be used to drain off the condensate. Note that the embodiment of FIG. 4, which may be described as a long axis serpentine alternate airflow pattern, will receive pressurized air as in the previous embodiments, but may use a typical prior art short fin evaporator with the fins kept vertical. This positioning allows water condensing on the fins to drop by gravity to the bottom airflow redirectors 46, where the condensate is collected into condensate collection tube 32 or tubes beneath as illustrated. By this means, all condensate is collected and eliminated from the evaporator, thus ensuring that a water trap in the evaporator cannot occur.

Note that with the location of the thermostatic expansion valve 40 that the airflow pattern has its entry to the evaporator coil 16 through the warmest portion of the heat exchanger or evaporator coil and its exit adjacent the thermostatic expansion valve is typically where the evaporator coil is coldest and working at maximum efficiency. The dividers and redirectors simply force the pressurized airflow back through the evaporator coil 16 repeatedly in order to achieve maximum heat extraction and the coldest air possible. Walls, encasements or a housing in the embodiment illustrated in FIG. 4 may be applied directly and sealed adjacent the short axis of the fins and engage the dividers and the airflow redirectors and endplates. As such, the short axis is blocked so that no airflow can flow through it and only long axis serpentine flow may be generated. Thus, walls are configured as illustrated in FIG. 4 to generate serpentine long axis flow pressurized through a coil and available to a personal air cooling device downstream of outlet 38.

Figure 5A:
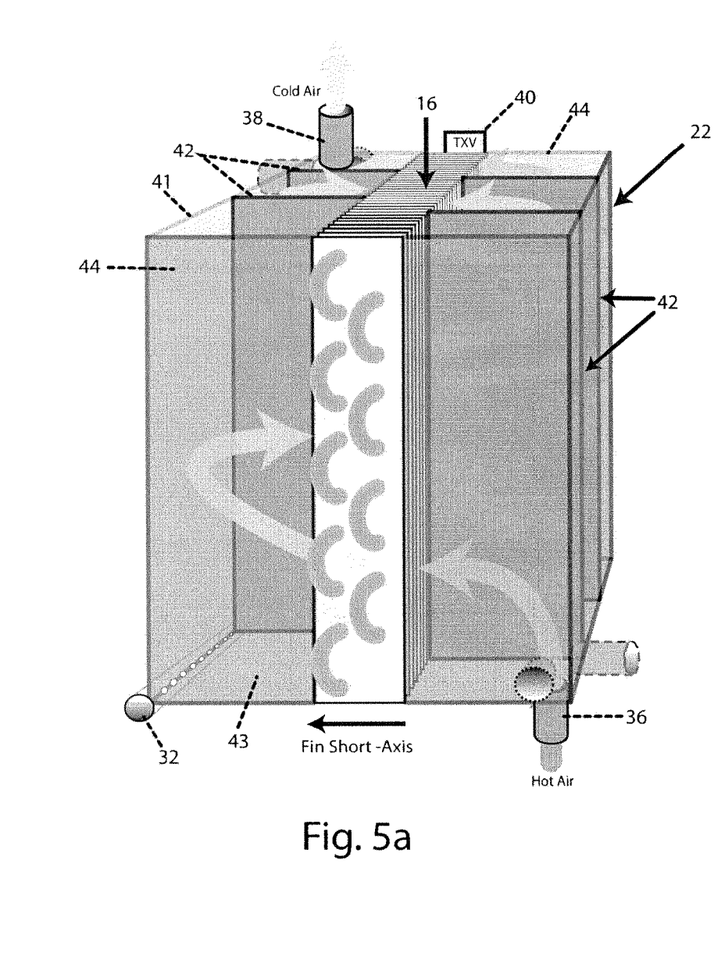
FIGS. 5A and 5B illustrate an end view in perspective and a top view, respectively, of another alternate embodiment of Applicant's evaporator.
Figure 5B:
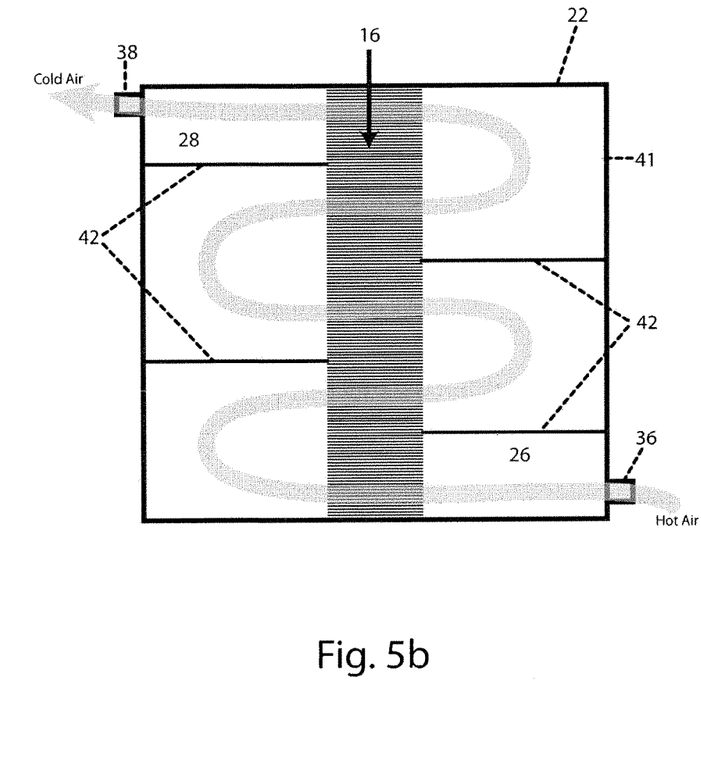

FIGS. 5A and 5B represent yet another use of walls configured to generate a serpentine (multiple pass) alternate airflow through an evaporator coil 16 comprising an evaporator 15 for use with a personal air cooling device. In FIGS. 5A and 5B, however, there is a serpentine flow across the short axis of a vertically oriented coil. Here, fins 18 of evaporator coil 16 are placed in a vertical orientation. Encasement or housing 22 partially includes a multiplicity of airflow redirectors 46 (external walls). Encasement housing 22 may have external walls acting as airflow redirectors 46. An upstream plenum 26 and a downstream plenum 28 is provided. As can be seen best in FIG. 5B, dividers 42 are staggered and are opposed so as to generate the serpentine airflow indicated by the arrows in FIG. 5B and the arrows in FIG. 5A. Note again cold air outlet 38 is adjacent thermostatic expansion valve 40. Collection tube 32 may be used and floor 43 may be cantered slightly so the condensate, draining from top to bottom as seen in FIG. 5A, may run slightly downhill to the left, engage collection tube, and can be removed from the encasement or housing 22.

Illustrated in FIGS. 5A and 5B, it can be seen that the encasement is engaged with dividers 42, which are used in conjunction with the side walls and end walls as indicated to help redirect airflow so it passes multiple times across different short axis sections of the coil. With the use of the dividers, the encasement, and the inlet/outlet, the serpentine motion causes the airstream to be repetitively chilled with a final result being cold airflow. Typically, humidity will condense on the air fins and run vertically to the bottom of the encasement. The typically sloping floor 43 delivers condensate to the collection tube 32. This water can be drained or, as the airflow is pressurized, can be blown onto the fans cooling the hot condenser heat exchanger. This will help cool the condenser more effectively while turning water condensate back into vapor which can be carried out in the airstream. Another effect is to increase the efficiency of the system as a whole.

Figure 6A:
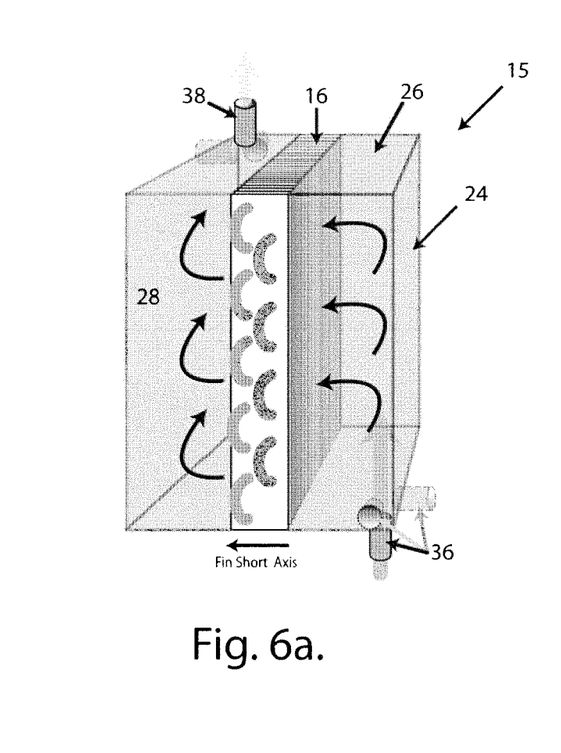
FIGS. 6A and 6B illustrate another alternate preferred embodiment of Applicant's evaporator.
Figure 6B:
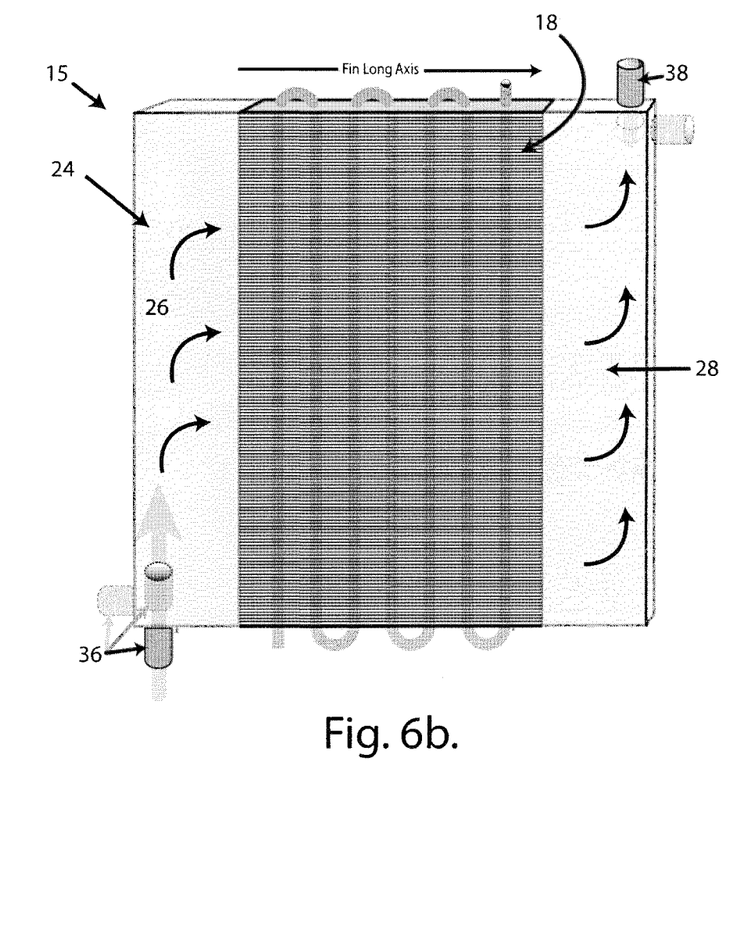

FIGS. 6A and 6B illustrate a short axis cross-counter flow (FIG. 6A) and along axis cross-counter flow (FIG. 6B) embodiment of evaporator 15. Cross-counter flow is another pressurized alternate pathway through evaporator 15 which results in greater heat extraction of the airstream passing through it as opposed to a normal, unpressurized single short axis pass through an evaporator. The inlet and the outlet are precisely in opposite positions on the housing surrounding the evaporator resulting in the most even distribution of airflow through the evaporator coil 16. In FIGS. 6A and 6B, inlet of warm pressurized air 36 is provided to upstream air plenum 36. Encasement or housing 24 is provided. In FIG. 6A, walls of the housing force air across the short axis, into downstream plenum 28, out outlet 38. In FIG. 6A, the fins are vertical, and in FIG. 6B, the fins are horizontal.

Figures 7A, 7B:
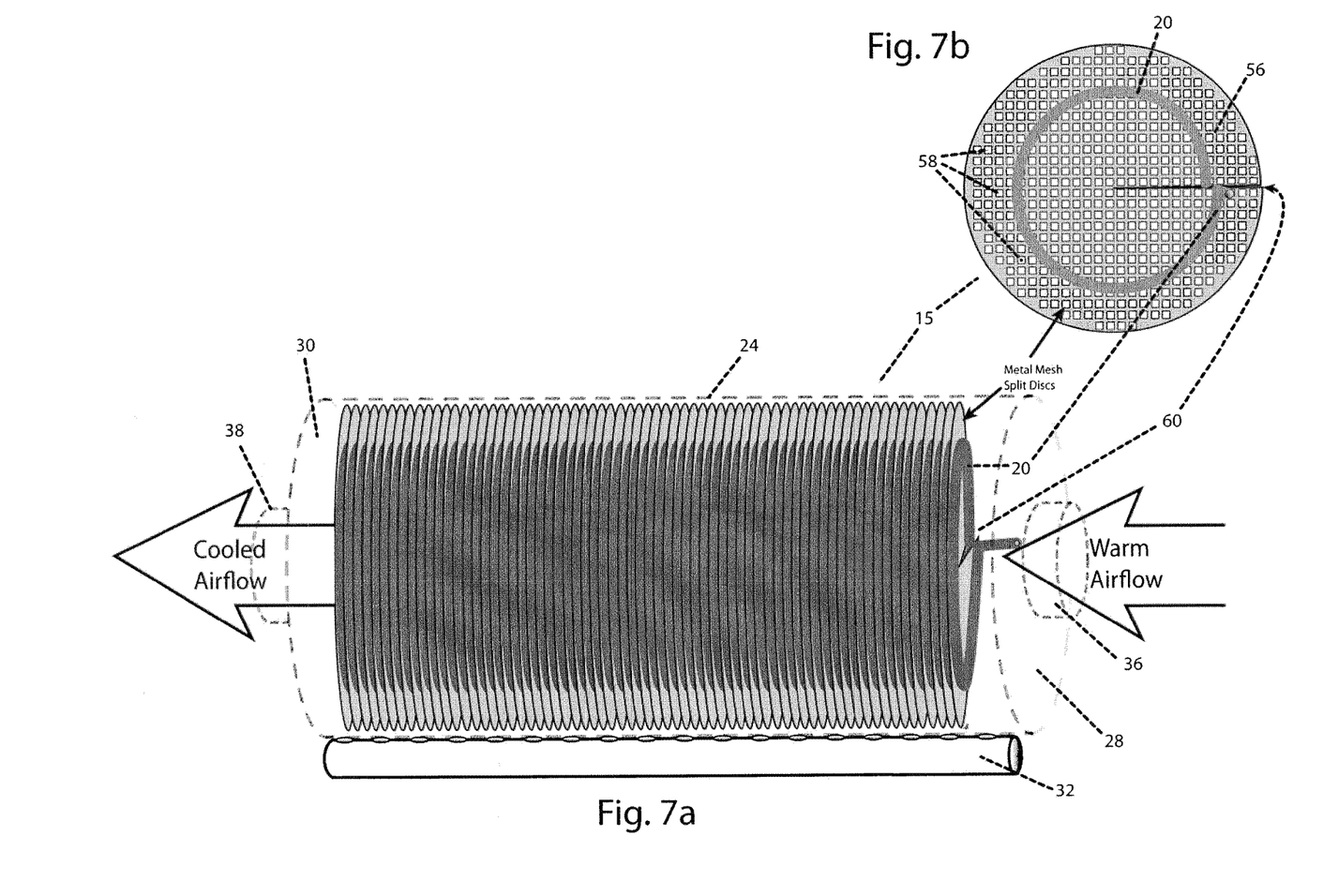
FIG. 7A illustrates a side perspective view of another alternate embodiment of Applicant's evaporator and FIG. 7B illustrates a side elevational view of a portion of the evaporator of FIG. 7A.

FIGS. 7A and 7B illustrate another embodiment of Applicant's evaporator. In this embodiment, the evaporator has multiple cylindrical disks 56 aligned parallel to one another and the disks having a multiplicity of openings 58 therein. The disks are physically contacted with a typically coiled coolant tube having an inlet at one end and an outlet at the other. An encasement is provided having a cylindrical side wall and typically planar end walls. The end walls will include an inlet and an upstream plenum and an outlet and a downstream plenum. The disks are typically maintained in a vertical position and there may be a collection tube at the lowest point of the cylindrical sidewall.

The spiraled or coiled effect is assisted in providing a slice at least partially through the disk and separating them slightly with a gap 60 in which the coiled coolant tubing can pass from one disk to the next. The spiraled or coiled airflow path is created by the intersecting of the split metal disks into a coil, or coaxial coils of different diameters, in the manner set forth in FIGS. 7A and 7B. While this device is a variation of lateral airflow path, the split disks will introduce some spiraling of the warm air entering the evaporator coil 16 from the upstream plenum. This device may be useful when constrained evaporator size dictate this designed smaller diameter. Air enters upstream plenum 28 through inlet 36 and percolates through the openings 58 with some rotation generated by gap 60 and cools as it passes through the cold mesh generated by the disks. Condensate may collect along the bottom cylindrical sidewall and pass through tube enclosure for draining.

Applicant's airflow in the embodiments illustrated, wherein the airflow is in contact with the fins, is typically at least 10 inches to achieve the relative humidity decrease necessary.

The following Figures of the '732 reference incorporated herein by reference show personal cooling devices 62 that lay on or adjacent the skin, and that are either worn by a user or lay on the user: FIGS. 21A, 21B, 21C, 22, 23A, 23B, 25A, 25B, 26, 27, 28, 29A, 29B, and 37. These include, typically, multiple tubes and multiple jets directed generally towards the skin of the wearer.

Figure 8:
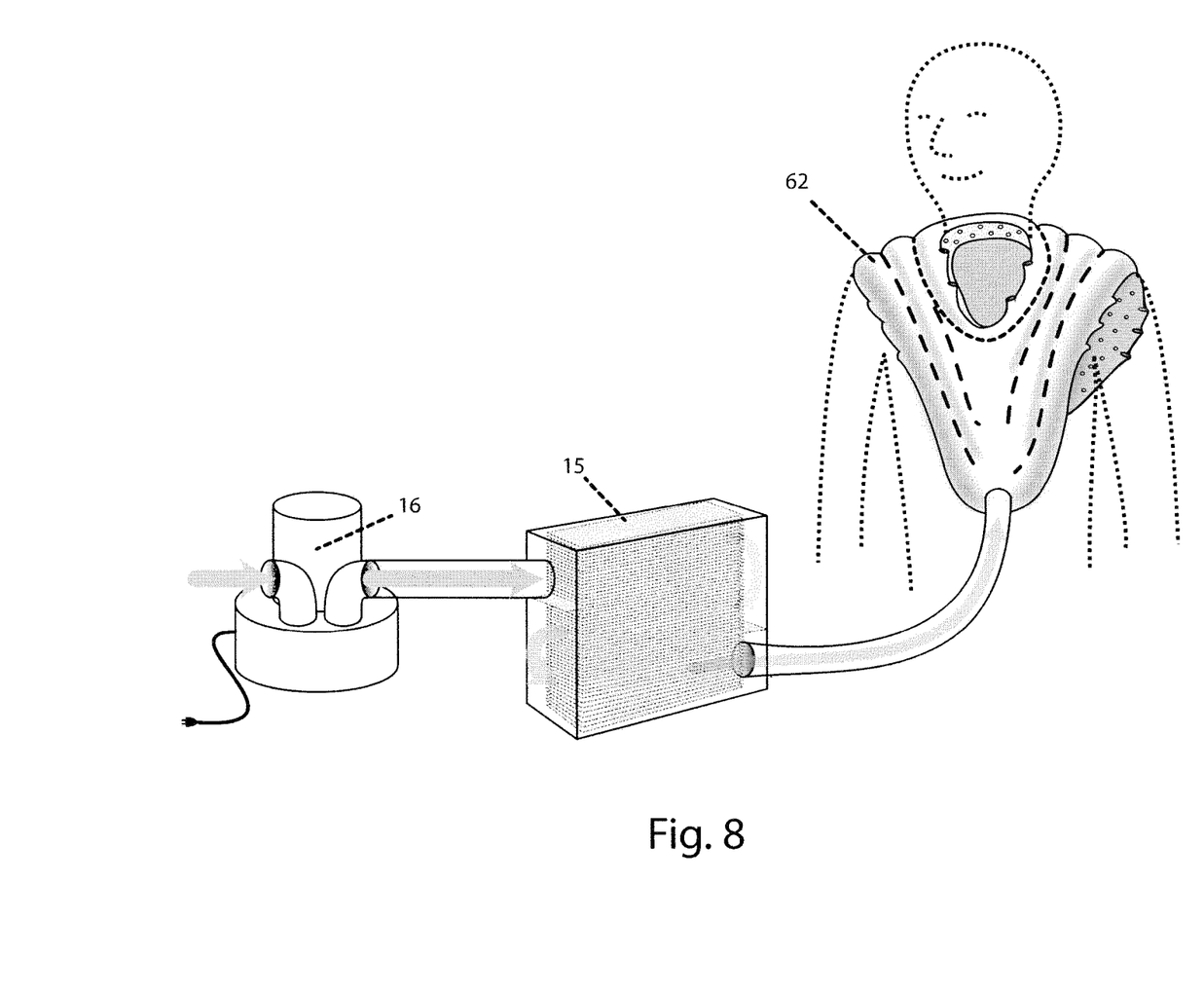
FIG. 8 illustrates Applicant's system comprising a blower box or other source of pressurized ambient air and an evaporator comprising one of the embodiments as set forth herein and a personal cooling device being worn by a person.

FIG. 8 illustrates Applicant's system comprising a blower box 64 or other source of pressurized ambient air and an evaporator comprising one of the embodiments as set forth herein and a personal cooling device 62 being worn by a person. Note in FIG. 8, the evaporator is shown, but other elements of the coolant circuit, such as the condenser and the like, are known in the art and represent, typically, a remote condenser for releasing heat.

Although the invention has been described in connection with the preferred embodiment, it is not intended to limit the invention's particular form set forth, but on the contrary, it is intended to cover such alterations, modifications, and equivalences that may be included in the spirit and scope of the invention as defined by the appended claims.

The invention claimed is:

1. A system for cooling a person, the system comprising:
a source for providing pressurized ambient air;
an evaporator having an evaporator coil comprising a multiplicity of tabular fins, the fins having a long axis and a short axis, the fins engaging a coolant line configured to receive a recirculating coolant that undergoes a phase change in the coolant line, the evaporator having a housing, the housing including an upstream plenum and a downstream plenum, the upstream plenum engaging at least part of the evaporator coil and having an inlet for engaging the pressurized ambient air from the pressurized ambient air source, the downstream plenum engaging at least another part of the evaporator coil, the downstream plenum including an outlet, the evaporator comprising a plurality of dividers to partition the fins into multiple groups through which the pressurized ambient air will pass sequentially while traversing through the evaporator and a plurality of U-shaped redirectors having curved interior walls to direct the pressurized ambient air exiting a group of fins to a next group of fins, the repeated passing of the pressurized ambient air over the groups of fins cooling pressurized ambient air having a temperature between 80 degrees F. and 110 degrees F. when entering the upstream plenum by at least 25 degrees F. during a single pass through the evaporator;
a tube for connecting the source to the inlet of the evaporator;
a personal cooling member, the personal cooling member including an inlet for receiving cooled air from the outlet of the evaporator, the personal cooling member configured to direct cooled air received from the evaporator to the wearer's face to provide surface and direct core-body cooling; and
a tube for connecting the personal cooling member to the outlet of the evaporator so as to confine the cooled air leaving the evaporator to the personal cooling member.

2. The system of claim 1, wherein the evaporator coil is adapted to maintain the fins vertically in the housing and the dividers are adapted to define a pressurized airstream between the inlet and outlet so as to provide a serpentine, single pass of the airstream with the coil; and wherein the dividers are further adapted to move the pressurized airstream along the long axis of the fins.

3. The system of claim 2, further including a condensation tube individually connected to multiple ones of the U-shaped redirectors beneath a lower end of the evaporator coil for draining condensate from the evaporator.

4. The system of claim 3, wherein at least one of the upstream plenum or downstream plenum is at least partly below the coil.

5. The system of claim 3, wherein both of the upstream plenum and the downstream plenum are at least partly above the coil.

6. The system of claim 1, wherein the evaporator coil is adapted to maintain the fins vertically in the housing and the dividers are adapted to define a pressurized airstream for making a single pass between the inlet and the outlet.

7. The system of claim 6, further including a condensation tube beneath a lower end of the evaporator coil for draining condensate from the evaporator.

8. The system of claim 1, wherein the evaporator includes multiple disk shaped cylindrical fins encased about said multiple disk shaped cylindrical fins' outer circumference by the housing, said multiple disk shaped cylindrical fins having a thickness less than said multiple disk shaped cylindrical fins' diameter and a multiplicity of openings therethrough to allow pressurized ambient air to flow through said multiple disk shaped cylindrical fins transverse to the diameter of said multiple disk shaped cylindrical fins, the evaporator configured to direct pressurized ambient air toward said multiple disk shaped cylindrical fins transverse to the diameter of said multiple disk shaped cylindrical fins.

9. The system of claim 8, further including a condensation tube beneath a lower end of the evaporator coil for draining condensate from the evaporator.

10. The system of claim 8, wherein the fins comprise a center section comprising a plurality of the openings configured to allow the pressurized ambient air to flow through said multiple disk shaped cylindrical fins transverse to the diameter of said multiple disk shaped cylindrical fins, said center sections further comprising a slit extending radially from a center section, the slit configured to engage the evaporator coil.

11. The system of claim 1, wherein the personal cooling member includes at least some walls defining tubes adapted to conform to the user's torso, the tubes including multiple jets directed at the torso of the user.

12. The system of claim 11, wherein the personal cooling member includes a helmet with a tube for receiving cool air, the tube directing the cool air to the face of the wearer.

13. The system of claim 12, wherein the personal cooling member is configured to provide only single pass of cool air.

14. The system of claim 1, wherein the personal cooling member exhausts cooled air to the environment.

15. The system of claim 1, wherein the long axis of the fins is oriented vertically.

16. The system of claim 1, wherein the evaporator is configured such that the pressurized ambient air flows repeatedly along the long axis of the fins during a single pass through the evaporator.

17. The system of claim 1, wherein the evaporator is configured such that the coils are maintained above 32 degrees F.

18. The system of claim 1, further comprising a condensate collector, a condenser comprising cooling fins, and a tube coupling the condensate collector to the condenser such that the condensate is blown onto the condenser's cooling fins by air pressure in the evaporator.

19. The system of claim 1, wherein the evaporator contains a single coolant line, the coolant line configured such that said coolant line winds repeatedly through the fins, and the pressurized ambient air being cooled exits from the fins in the downstream plenum where the coolant line enters the housing.

20. A system for cooling a person, the system comprising:
a source for providing pressurized ambient air;
an evaporator having an evaporator coil comprising a multiplicity of tabular fins, the fins having a long axis and a short axis, the fins engaging a coolant line configured to receive a recirculating coolant that undergoes a phase change in the coolant line, the evaporator having a housing and a condensate collector, the housing including an upstream plenum and a downstream plenum, the upstream plenum engaging at least part of the evaporator coil and having an inlet for engaging the pressurized ambient air from the pressurized ambient air source, the downstream plenum for engaging at least another part of the evaporator coil, the downstream plenum including an outlet, the evaporator comprising a plurality of dividers to partition the fins into multiple groups through which the pressurized ambient air will pass sequentially while traversing through the evaporator and a plurality of U-shaped redirectors having curved interior walls to direct the pressurized ambient air exiting a group of fins to a next group of fins, the repeated passing of the pressurized ambient air over the groups of fins cooling pressurized ambient air having a temperature between 80 degrees F. and 110 degrees F. when entering the upstream plenum by at least 25 degrees F. during a single pass through the evaporator;

a tube for connecting the source to the inlet of the evaporator;

a flexible personal cooling member with at least some walls conforming to a user's torso adapted to lay on the user, the personal cooling member comprising multiple tubes and multiple jets on at least some of the multiple tubes, the personal cooling member including an inlet for receiving cooled air from the outlet of the evaporator, the personal cooling member including walls configured to distribute cooled air received from the evaporator to the tubes and the jets and to the wearer's face to provide surface and direct core-body cooling; and a tube for connecting the personal cooling member to the outlet of the evaporator so as to confine the cooled air leaving the evaporator to the personal cooling member;

wherein the evaporator coil is adapted to maintain the fins vertically in the housing and the dividers are adapted to define a pressurized airstream between the inlet and outlet so as to provide a serpentine, single pass of the airstream with the coil;

wherein the dividers are further adapted to move the pressurized airstream along the long axis of the fins; and further including a condensation tube beneath a lower end of the evaporator coil for draining condensate from the evaporator.

\* \* \* \* \*